United States Patent
Takeda (10) Patent No.: US 6,826,359 B1
(45) Date of Patent: Nov. 30, 2004

(54) FUNDUS CAMERA

(75) Inventor: Takanori Takeda, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 730 days.

(21) Appl. No.: 09/704,125

(22) Filed: Nov. 1, 2000

Related U.S. Application Data (63) Continuation of application No. PCT/JP00/02767, filed on Apr. 27, 2000.

(30) Foreign Application Priority Data

Apr. 27, 1999 (JP) .......................................... 11-119157

(51) Int. Cl.⁷ .............................................. G03B 29/00
(52) U.S. Cl. ............................ 396/18; 351/206; 348/78
(58) Field of Search ............................ 396/18; 348/78; 351/206

(56) References Cited

U.S. PATENT DOCUMENTS

| | | | | |
|---|---|---|---|---|
| 3,893,447 A | * | 7/1975 | Hochheimer et al. | ........ 351/206 |
| 5,118,179 A | * | 6/1992 | Sano et al. | .................. 351/206 |
| 6,456,787 B1 | * | 9/2002 | Matsumoto et al. | .......... 396/18 |

FOREIGN PATENT DOCUMENTS

| | | | |
|---|---|---|---|
| JP | 6-277185 | 3/1993 | ............ A61B/3/14 |
| JP | 8-256988 | 3/1995 | ............ A61B/3/14 |
| JP | 9-135814 | 11/1995 | ............ A61B/3/14 |

* cited by examiner

*Primary Examiner*—David Gray
(74) *Attorney, Agent, or Firm*—Chapman and Cutler LLP (57) ABSTRACT

A fundus camera comprising TV relay lens unit (27) and a body unit (1) which is capable of mounting plurality of TV cameras (30, 31) and (32) is provided. The body unit (1) includes photographing optical system (3) for photographing a fundus Fu to be observed. The TV relay lens unit (27) is detachably mountable on the body unit (1) and has a function to direct a fundus image forming luminous flux divided by the photographing optical system (3) to respective TV camera according to light. The TV relay lens unit (27) comprises a switching mirror (37) and a reflecting optical element (38) so as to adapt to TV cameras of a visible-fluorescent photographing/infrared-fluorescent photographing TV camera (30) which has sensitivity for both visible light and infrared light, a color photographing TV camera (31), which has sensitivity for visible light and a fundus observing TV camera (32) which has sensitivity for infrared light. The switching mirror (37) and the reflecting optical element (38) selectively switches the optical path of fundus image forming luminous flux so as to direct it to respective TV camera according to light by instantaneous insertion or retraction operation.

7 Claims, 6 Drawing Sheets

FIG. 6

FUNDUS CAMERA

CROSS REFERENCE TO RELATED APPLICATION

This is a continuation of PCT Application No. PCT/JP00/02767, filed Apr. 27, 2000.

BACKGROUND OF THE INVENTION

1. Field of the invention

The present invention relates to an improvement of fundus camera which photographs an image of fundus and more particularly relates to an improvement of fundus camera through which colored fundus images, visible-fluorescent fundus images and infrared-fluorescent fundus images are photographed by Television (hereinafter referred to as "TV") camera.

2. Description of the Related Art

In fundus photographing, because infrared-fluorescent image cannot be photographed by conventional 35 mm film camera or instant camera, TV camera which converts infrared-fluorescent light into TV signal has been generally used for this purpose. Also a 35 mm film camera has been usually employed for photographing colored fundus images and visible-fluorescent images due to its higher resolution. Recently, instead of 35 mm film camera, TV camera is getting popular for photographing visible-fluorescent images and colored images as resolution of CCD for TV camera has been improved.

Meanwhile, with regard to infrared-fluorescent photographing, visible-fluorescent photographing and colored photographing, plurality of TV cameras must be selectively exchanged in accordance with a selection a photographing made, as the wavelength, amount of light or necessary resolution differs according to a selected photographing. Further, because several types of specific designed relay lens units are individually required to adapt respective TV cameras to the fundus camera body, each relay lens unit for respective TV cameras must be exchanged at the same time. To exchange TV camera and its relay lens unit according to the light of photograph is troublesome but inevitable work.

For this problem, the Japanese Patent Application Laid Open Hei 8-256988 proposed a fundus camera in which an optical path length adjusting member is arranged within a TV relay lens unit in order to adjust change of light path length depending on the type of photographing. By this arrangement, the relay lens unit need not be exchanged. However, as TV cameras themselves must be exchanged, it is still inconvenient for users.

The present invention is proposed to solve the above problem and an object of the present invention is to provide a fundus camera having improved operationality which makes it unnecessary to exchange TV camera for fundus photographing.

SUMMARY OF THE INVENTION

In accordance with the first aspect of present invention, a fundus camera comprising a body unit having photographing optical system to photograph a fundus to be observed, and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected, and a color photographing TV camera having sensitivity for visible light, wherein said TV relay lens unit is equipped with a switching mirror which is retractably and insertably arranged in an optical path of said fundus image forming luminous flux for switching said color photographing TV camera and said visible-fluorescent photographing/infrared-fluorescent photographing TV camera in accordance with the photographing mode, and a reflecting optical element which is arranged between said switching mirror and said color photographing TV camera to direct said fundus image forming luminous flux to said fundus observing TV camera, and said switching mirror is retracted from the optical path of said fundus image forming luminous flux to direct said flux to said fundus observing TV camera for observing a fundus in said infrared-fluorescent photographing mode, and said switching mirror is instantaneously inserted into said optical path to direct said fundus image forming luminous flux to said visible-fluorescent photographing/infrared-fluorescent photographing TV camera for photographing the fundus in said infrared-fluorescent photographing mode, is provided.

According to the second aspect of the invention, a fundus camera of the above described first aspect further characterized in that said reflecting optical element is a dichroic mirror which is selectively passing visible light and reflecting infrared light, is provided.

According to the third aspect of the invention, a fundus camera of the above described first aspect further characterized in that said reflecting optical element is a half mirror, is provided.

According to the fourth aspect of the invention, a fundus camera of the above described first aspect further characterized in that said reflecting optical element is a switching mirror which is insertably or retractably arranged in said optical path to direct said fundus image forming luminous flux to said fundus observing TV camera when it is inserted in said optical path, is provided.

According to the fifth aspect of the invention, a fundus camera comprising a body unit having photographing optical system to photograph a fundus to be observed, and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected, and a color photographing TV camera having sensitivity for visible light, and wherein said TV relay lens unit is equipped with first switching mirror which is retracted from the optical path of said fundus image forming luminous flux to direct said fundus image forming luminous flux to said the observing TV camera when infrared-fluorescent photographing mode is selected and the observation thereof is conducted and is instantaneously inserted into the optical path of said fundus image forming luminous flux to direct said fundus image forming luminous flux to said visible-fluorescent photographing/infrared-fluorescent photographing TV camera for infrared-fluorescent photographing mode when photographing the fundus, and second switching mirror which is inserted into the optical path of said fundus image forming luminous flux when color photographing mode is selected, and is retracted from the optical path of said fundus image forming luminous flux when visible-fluorescent photographing mode is selected, is provided.

According to the sixth aspect of the invention, a fundus camera comprising a body unit having photographing optical system to photograph a fundus to be observed, and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected and a color photographing TV camera having sensitivity for visible light, and wherein said TV relay lens unit is equipped with first switching mirror which is inserted into the optical path of said fundus image forming luminous flux to direct said fundus image forming luminous flux to said observing TV camera when infrared-fluorescent photographing mode is selected and the observation thereof is conducted, and is instantaneously retracted from the optical path of said fundus image forming luminous flux to direct said fundus image forming luminous flux to said visible-fluorescent photographing/infrared-fluorescent photographing TV camera for infrared-fluorescent photographing mode when photographing the fundus, and second switching mirror which is inserted into the optical path of said fundus image forming luminous flux when color photographing mode is selected and is retracted from the optical path of said fundus image forming luminous flux when visible-fluorescent photographing mode is selected, is provided.

According to the seventh aspect of the invention, a fundus camera comprising a body unit having photographing optical system to photograph a fundus to be observed, and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected and a color photographing TV camera having sensitivity for visible light, and wherein said TV relay lens unit is equipped with first switching mirror which is inserted into the optical path of said fundus image forming luminous flux to direct said fundus image forming luminous flux to said observing TV camera when infrared-fluorescent photographing mode is selected and observation thereof is conducted, and is instantaneously retracted from the optical path of said fundus image forming luminous flux to direct said fundus image forming luminous flux to said visible-fluorescent photographing/infrared-fluorescent photographing TV camera for infrared-fluorescent photographing mode when photographing the fundus, and second switching mirror which is retracted from the optical path of said fundus image forming luminous flux when color photographing mode is selected and is inserted into the optical path of said fundus image forming luminous flux when visible-fluorescent photographing mode is selected, is provided.

In a fundus camera according to the present invention, as the switching mirror is retracted from the optical path of said fundus image forming luminous flux when color photographing mode is performed by the color photographing TV camera, the visible light component of fundus image forming luminous flux is directed to the reflecting optical element and passed through it to the color photographing TV camera.

And when visible-fluorescent photographing mode is performed by visible-fluorescent photographing/infrared-fluorescent photographing TV camera, as the switching mirror is inserted into the optical path of fundus image forming luminous flux, the visible-fluorescent component of fundus image forming luminous flux is reflected by the switching mirror and directed to the visible-fluorescent photographing/infrared-fluorescent photographing TV camera.

Further, when infrared-fluorescent photographing mode is performed by the visible-fluorescent photographing/infrared-fluorescent photographing TV camera, as the switching mirror is retracted from the optical path of fundus image forming luminous flux when observing a fundus, the infrared-fluorescent component of fundus image forming luminous flux is directed to the reflecting optical element and reflected by it to the fundus observing TV camera, and when photographing the fundus as the switching mirror is instantaneously inserted into the optical path of fundus image forming luminous flux, the infrared-fluorescent component of fundus image forming luminous flux is reflected by the switching mirror and directed to the visible-fluorescent photographing/infrared-fluorescent photographing TV camera.

As described above, because the switching mirror moves according to respective photographing mode and directs the fundus image forming luminous flux to respective TV cameras which are used when each photographing mode is selected, the fundus camera provided in accordance with the present invention has higher operationality which makes it unnecessary to detach one and to mount another for exchange of TV camera for fundus photographing according to light.

BRIEF DESCRIPTION OF THE DRAWINGS

In the detailed description of the invention presented below, reference made to the accompanying drawing, in which.

DETAILED DESCRIPTION OF THE PREFERRED EMBODIMENT

Preferred embodiment of the fundus camera in accordance with the present invention is hereinafter described in detail with reference to the accompanying drawings.

Figure 1:
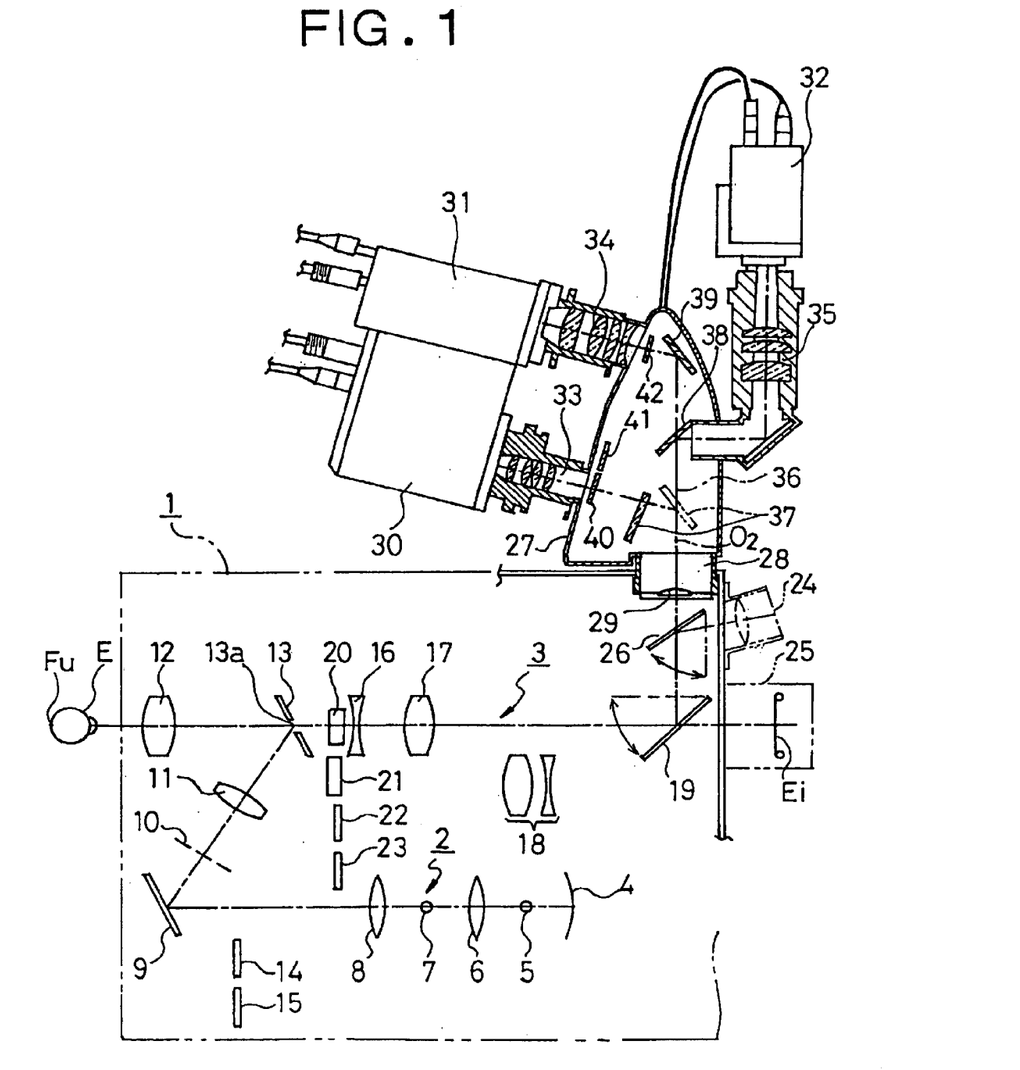
FIG. 1 is a side view with cross-section in part of an Embodiment and its Modifications No. 1 and No. 1' of fundus cameras in accordance with the present invention showing elementary disposition.

In FIG. 1, a body of fundus camera is shown with reference number 1. The fundus camera body 1 is mainly constituted by an illuminating optical system 2 for illuminating a fundus Fu to be observed and photographing optical system 3 which photographs the fundus Fu.

As shown in FIG. 1, the illuminating optical system 2 comprises concave reflecting mirror 4, a halogen lamp 5 for illuminating the fundus of eye E when it is observed, relay lens 6, a xenon tube 7 for illuminating the fundus when it is photographed, a condenser lens 8, a reflecting mirror 9, a ring-slit 10, a relay lens 11, a perforated mirror 13 and an objective lens 12, and they are arranged in this order. Further, in the light path of the illuminating system 2, an exciter filter 14 for visible-fluorescent photographing and an exciter filter 15 for infrared-fluorescent photographing are insertably and retractably arranged between a condenser lens 8 and a reflecting mirror 9. Herein, the perforated mirror 13 and the objective lens 12 are shared by a photographing optical system which will be described later.

Illuminating light from the halogen lamp 5 is directed through the relay lens 6, the condenser lens 8, the reflecting mirror 9, the ring-slit 10 and the relay lens 11 to the perforated mirror 13. After reflected by the perforated mirror 13, the light goes through the objective lens 12 and arrives at a fundus Fu of the eye E to be observed. The exciter filter 14 for visible-fluorescent photographing is inserted into this illuminating light path when photographing utilizing visible-fluorescent light is conducted (hereinafter referred to as "visible-fluorescent photographing mode") and the exciter filter 15 for infrared-fluorescent photographing is inserted when photographing utilizing infrared-fluorescent light is conducted (hereinafter referred to as "infrared-fluorescent photographing mode"). Both exciter filters 14 and 15 are retracted from the light path when photographing utilizing usual visible light is conducted (hereinafter referred to as "color photographing mode").

The photographing optical system 3 comprises the objective lens 12, the perforated mirror 13, a focusing lens 16, an image-forming lens 17 and a quick return mirror 19, and they are arranged in this order. Further in the photographing optical path of this optical system 3, optical path length adjusting filters 20 and 21, a barrier filter 22 for visible-fluorescent photographing mode and a barrier filter 23 for infrared-fluorescent photographing mode are insertably and retractably arranged between the perforated mirror 13 and the focusing lens 16. In addition, a variable power lens 18 is insertably and retractably arranged between the image-forming lens 17 and the quick return mirror 19. The perforated mirror 13 and the objective lens 12 are shared by the illuminating optical system 2 as explained above.

A luminous flux from the fundus Fu (hereinafter referred to as "fundus image forming luminous flux") is directed through the objective lens 12 and a hole 13a of perforated mirror 13, to focusing lens 16 and image-forming lens 17. Optical path length adjusting filter 20 and 21 are inserted into and/or retracted from the photographing optical path to correct an optical path length caused by a difference of wavelength between respective photographing modes. The visible-fluorescent barrier filter 22 is inserted into the optical path to use when visible-fluorescent photographing mode is selected, and the infrared-fluorescent barrier filter 23 is inserted to use when infrared-fluorescent photographing mode is selected. Both of them are retracted when color photographing mode is performed. The variable power lens 18 is inserted into the optical path of the photographing optical system 3 when a magnified image of the fundus Fu is observed or photographed.

In the fundus camera body 1, an eyepiece 24 and a 35 mm film camera 25 are arranged and especially the latter is detachable. The 35 mm film camera 26 is arranged on an extending line of the photographing optical path, and at the opposite side from the image-forming lens 17 with respect to the quick return mirror 19, and is arranged so that the luminous flux from the fundus Fu is directed thereto, when the quick return mirror 19 is retracted from the photographing optical path as shown in FIG. 1 by double dotted broken line. Therefore, the quick return mirror 19 is instantaneously retracted from the photographing optical path when the 35 mm film camera 25 is used but it is usually remained in the optical path other than the 35 mm camera is used.

A quick return mirror 26 is inserted into the optical path when the quick return mirror 19 is inserted into the optical path. The eyepiece 24 is arranged in a reflection optical path of the quick return mirror 26. Therefore, the quick return mirror 26 is inserted in the reflecting optical path of the quick return mirror 19 when the eyepiece 24 is used to observe the fundus Fu, but it remains out of the optical path as shown in FIG. 1 by double dotted broken line when the eyepiece 24 is not used to observe the fundus Fu, or, TV camera 32 is used to observe the fundus Fu. The eyepiece 24 is used when color photographing mode is selected and when the visible-fluorescent photographing mode is selected.

A unit mounting portion 28 is arranged with a field lens 29 at upper portion of the fundus camera body 1. A TV relay lens unit 27 is detachably mounted on the fundus camera body 1 through the unit mounting portion 28. A fundus image forming luminous flux which is reflected by the quick return mirror 19 is temporarily focused near by the field lens 29 and then directed into the TV relay lens unit 27 when the quick return mirror 26 is retracted from the optical path.

In the TV relay lens unit 27, a still image recording TV camera 30 for still image recording of the visible-fluorescent fundus image and the infrared-fluorescent fundus image (hereinafter referred to as "visible-fluorescent photographing/infrared-fluorescent photographing TV camera"), a color photographing TV camera 31 for still image recording of the visible light fundus image and an observing TV camera 32 to observe infrared-fluorescent fundus image (hereinafter referred to as "fundus observing TV camera") are arranged. And each TV camera has respective TV relay lens 33, 34 and 35. The fundus image forming luminous flux is divided by a dichroic mirror 38 as a reflecting optical element (described later in detail) and directed to the observing TV camera 32. As the divided fundus image forming luminous flux lessens its quantity of luminous flux, sensitivity of observing TV camera 32 is greater than that of the still image recording TV camera 30.

On the optical path of the fundus image forming luminous flux (hereinafter referred to as "optical path O2") within the TV relay lens unit 27, a switching mirror 37 having a function as quick return mirror, the dichroic mirror 38 and a reflecting mirror 39 are arranged in this order from the field lens 29. The dichroic mirror 38 is an optical element for selectively reflecting infrared light and passing visible light and the reflecting mirror 39 is for reflecting all kind of lights as described in detail later. The switching mirror 37 is arranged in order to direct the fundus image forming luminous flux to the still image recording TV camera 30 when it is inserted into the optical path O2 as shown in FIG. 1 by double dotted broken line. The dichroic mirror 38 divides the fundus image forming luminous flux into visible light and infrared light. That is, it passes selectively the visible light component, directing it to the reflecting mirror 39, and reflects selectively the infrared light component, directing it to the observing TV camera 32.

The switching mirror 37 is retracted from the optical path O2 when color photographing mode by color photographing TV camera 31 is selected. When observing a fundus Fu, the quick return mirror 19 and 26 are inserted into the optical path O2. Thus, a fundus image forming luminous flux from Fundus Fu is directed to the eyepiece 24, the fundus Fu can be observed at the eyepiece 24. For photographing the fundus Fu, the quick return mirror 26 is instantaneously retracted from the reflecting optical path when a shutter releasing button (not shown) is operated. As the switching mirror 37 is also already retracted, the fundus image forming luminous flux is directed to the dichroic mirror 38. The visible light component of fundus image forming luminous flux passes through the dichroic mirror 38 and is reflected by the reflecting mirror 39 and directed into the color photographing TV camera 31. An optical path length adjusting filter 42 is arranged on the light path before the TV relay lens 34 of color photographing TV camera 31. The optical path length adjusting filter 42 has a function to correct a difference of optical path according to respective photographing mode. Just as the optical path length adjusting filter 20 and 21, the filter 42 is inserted automatically into the optical path when color photographing mode is selected. In this way photographing of the visible light fundus image by the color photographing TV camera 31 is accomplished.

The switching mirror 37 is inserted into the optical path O2 when visible-fluorescent photographing mode, in which the still image recording TV camera 30 is used and the exciter filter 14 and barrier filter 22 are inserted into the optical path, is performed. When observing the fundus Fu, the quick return mirror 19 and 26 are inserted into the optical path O2. In this way, a fundus image forming luminous flux from Fundus Fu is directed to the eyepiece 24 and can be observed at the eyepiece 24. For photographing the fundus Fu, the quick return mirror 26 is instantaneously retracted from the reflecting optical path when the shutter releasing button (not shown) is operated. As the switching mirror 37 is also inserted in advance, the fundus image forming luminous flux is reflected and directed to the still image recording TV camera 30. Optical path length adjusting filter 40 and 41 are arranged on the light path before the TV relay lens 33 of color photographing TV camera 30. The respective optical path length adjusting filter 40 and 41 have the function to correct the difference of optical path length caused by the difference of wavelength of utilized light according to respective photographing mode just as the optical path length adjusting filter 20 and 21, the optical path length adjusting filter 40 is inserted automatically into the optical path when visible-fluorescent photographing mode is selected. In this way, photographing of the visible-fluorescent fundus image by the still image recording TV camera 30 is accomplished.

The switching mirror 37 is retracted from the optical path O2 when infrared-fluorescent photographing mode, in which the still image recording TV camera 30 is used and the exciter filter 15 and barrier filter 23 are inserted into the optical path, is performed. When observing the fundus Fu, the quick return mirror 19 is inserted into the optical path O2 while the quick return mirror 26 and the switching mirror 37 are retracted from the optical path. Thus, a fundus image forming luminous flux from Fundus Fu is reflected by the quick return mirror 19 and directed to the dichroic mirror 38. The infrared component of fundus image forming luminous flux is reflected by the dichroic mirror 38 and directed into the observing TV camera 31, then, the fundus Fu can be observed at the observing TV camera 31. For photographing the fundus Fu, the switching mirror 37 which has also the function of quick return mirror is instantaneously inserted into the optical path O2 when the shutter releasing button (not shown) is operated. Thus, the fundus image forming luminous flux is reflected and directed to the still image recording TV camera 30. Optical path length adjusting filters 40 and 41 are arranged on the light path before the TV relay lens 33 of color photographing TV camera 30. The optical path length adjusting filter 41 is inserted automatically into the optical path when infrared-fluorescent photographing mode is selected. In this way, photographing of the infrared-fluorescent fundus image by the still image recording TV camera 30 is accomplished.

Modification 1

In the above described embodiment of the present invention, the dichroic mirror 38 is employed as the reflecting optical element between the switching mirror 37 and the reflecting mirror 39, however, a half mirror can be applicable instead of the dichroic mirror 38.

In this case, when color photographing mode is selected, the switching mirror 37 is retracted from the optical path O2 and the fundus image forming luminous flux is directed to the color photographing TV camera 31.

When visible-fluorescent photographing mode is selected, the switching mirror 37 is inserted into the optical path O2 and the fundus image forming luminous flux is directed to the still image recording TV camera 30.

When infrared-fluorescent photographing mode is selected and the fundus Fu is observed, the switching mirror 37 is retracted from the optical path O2 and the infrared-fluorescent fundus image is directed to the observing TV camera 32. When photographing the fundus Fu under the infrared-fluorescent photographing mode, the switching mirror 37 as the quick return mirror is instantaneously inserted into the optical path O2 in response to the operation of the shutter releasing button (not shown), and the infrared-fluorescent fundus image is directed to the still image recording TV camera 30.

Modification 1'

In the above described embodiment, the dichroic mirror 38 is arranged as the reflecting optical element between the switching mirror 37 and reflecting mirror 39. Instead of the dichroic mirror 38, another switching mirror can be utilized as a reflecting optical element 38 in the optical path O2.

In this case, when color photographing mode is selected, the switching mirror 37 and the switching mirror 38 are retracted from the optical path O2 and the fundus image forming luminous flux is directed to the color photographing TV camera 31.

When visible-fluorescent photographing mode is selected, the switching mirror 37 is inserted into the optical path O2 and the fundus image forming luminous flux is directed to the still image recording TV camera 30.

When infrared-fluorescent photographing mode is selected and the fundus Fu is observed, the switching mirror 37 is retracted from the optical path O2 while the switching mirror 38 is inserted into the optical path O2 and the infrared-fluorescent fundus image is directed to the observing TV camera 32. When photographing the fundus Fu under the infrared-fluorescent photographing mode, the switching mirror 37 which has also the function of quick return mirror is instantaneously inserted into the optical path O2 in response to the operation of the shutter releasing button (not shown), and the infrared-fluorescent fundus image is directed to the still image recording TV camera 30.

The eyepiece 24 can be omitted by means of changing the observing TV camera 32 into a TV camera which has sensitivity for both of visible light and infrared light and giving the switching mirror 38 the function of quick return mirror.

Modification 2

In the above described embodiment of the present invention, the dichroic mirror 38 is employed as the optical element in order to reflect infrared light component and to transmit the visible light component, and the observing TV camera 32 is arranged on the direction of reflection, while the color photographing TV camera 31 is arranged on the direction of transmittance. However, the dichroic mirror 38 can be selected from another optical element that has a function of reflecting visible light component and transmitting infrared light component.

Figure 2:
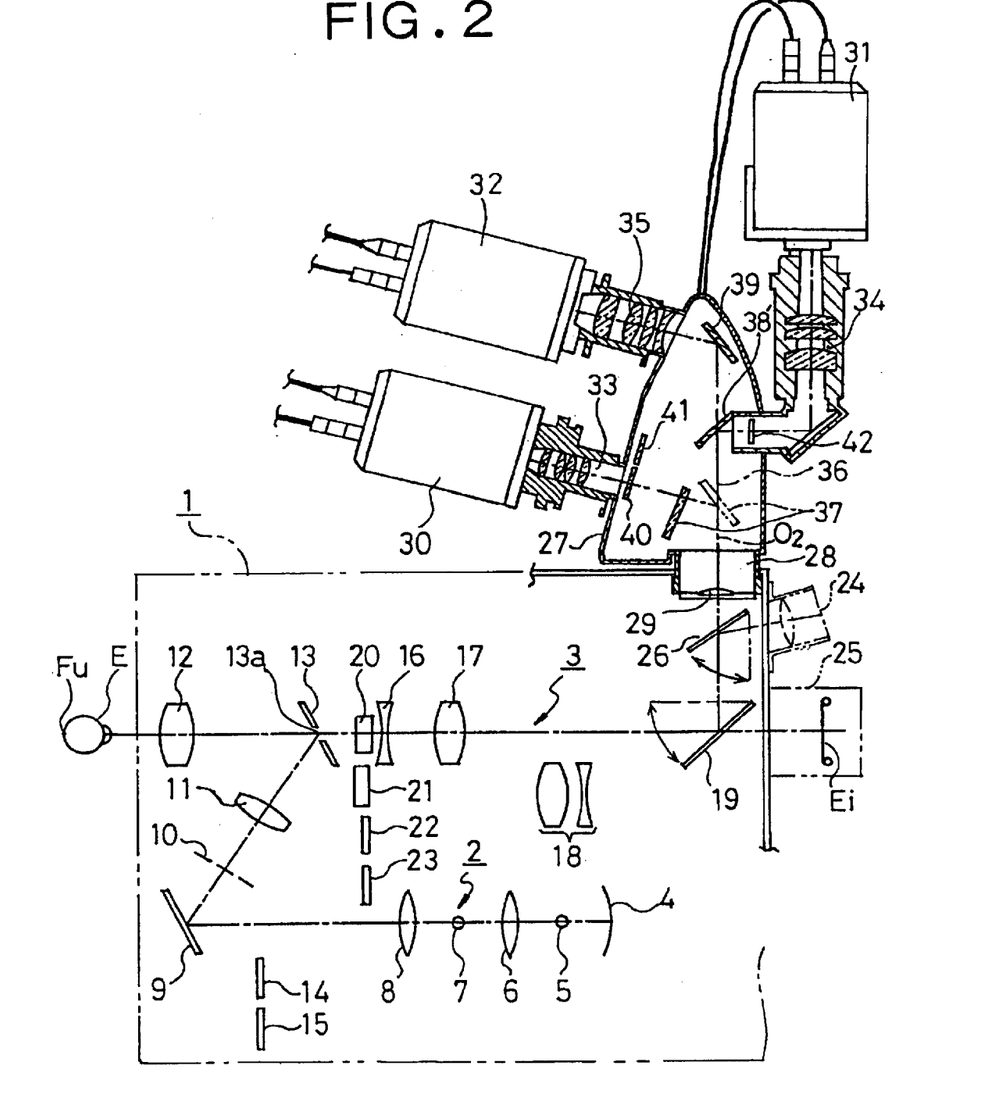
FIG. 2 is a side view with cross-section in part of a Modification No. 2 of fundus camera in accordance with the present invention showing elementary disposition.

In this case, within the TV relay lens unit 27, a switching mirror 37, dichroic mirror 38', and the reflecting mirror 39 are arranged in this order from the field lens 29 as shown in FIG. 2. The still image recording TV camera 30, the color photographing TV camera 31 and the observing TV camera 32 are attached to the body of TV relay lens unit 27 in this order from bottom to top. In the fundus camera in accordance with this Modification 2 the switching mirror 37 is retracted from the optical path and the visible light component of the fundus image forming luminous flux is directed to the color photographing TV camera 31 when color photographing mode is selected.

When visible-fluorescent photographing mode is selected, the switching mirror 37 is inserted into the optical path O2 and the fundus image forming luminous flux is directed to the still image recording TV camera 30.

When infrared-fluorescent photographing mode is selected and the fundus Fu is observed, the switching mirror 37 is retracted from the optical path O2 and the infrared-fluorescent fundus image is directed to the observing TV camera 32. When photographing the fundus Fu under the infrared fluorescent mode, the switching mirror 37 as the quick return mirror is instantaneously inserted into the optical path O2 in response to the operation of the shutter releasing button (not shown) and the infrared-fluorescent fundus image is directed to the still image recording TV camera 30.

Modification 3

In the above described embodiments, the dichroic mirror 38 as the reflecting optical element is arranged between the switching mirror 37 and the reflecting mirror 39. However, another arrangement can be employed as described below.

Figure 3:
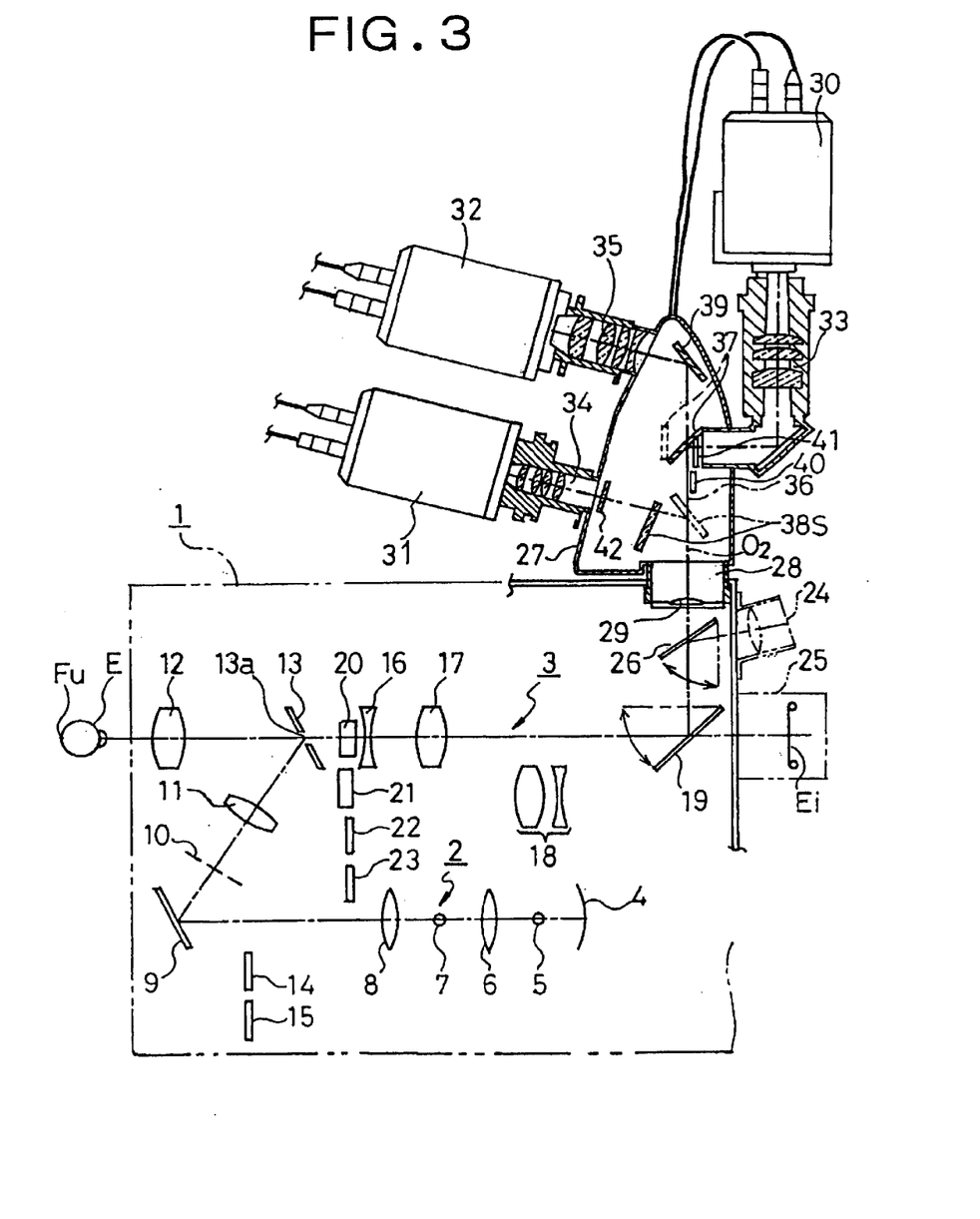
FIG. 3 is a side view with cross-section in part of a Modification No. 3 of fundus camera in accordance with the present invention showing elementary disposition.

In this case within the TV relay lens unit 27, switching mirror 38S, the switching mirror 37 and the reflecting mirror 39 are arranged in this order from bottom to top as shown in FIG. 3. The color photographing TV camera 31, the still image recording TV camera 30 and the observing TV camera 32 are attached to the body of TV relay lens unit 27 in this order from bottom to top.

In the fundus camera in accordance with this Modification 3 the switching mirror 38S is inserted into the optical path O2 and the fundus image forming luminous flux is directed to the color photographing TV camera 31 when color photographing mode is selected.

When visible-fluorescent photographing mode is selected, the switching mirror 37 is inserted into the optical path O2 and at the same time the switching mirror 38S is retracted from the optical path O2, then the fundus image forming luminous flux is directed to the still image recording TV camera 30.

When infrared-fluorescent photographing mode is selected and the fundus Fu is observed, the switching mirrors 37 and 38S are retracted from the optical path O2 and the infrared-fluorescent fundus image is directed to the observing TV camera 32. When photographing the fundus Fu under the infrared fluorescent photographing mode, the switching mirror 37 as the quick return mirror is instantaneously inserted into the optical path O2 in response to the operation of the shutter releasing button (not shown), and the infrared-fluorescent fundus image is directed to the still image recording TV camera 30.

Modification 4

The arrangement of still image recording TV camera 30 and observing TV camera 32 can be exchanged in the above described Modification 3.

Figure 4:
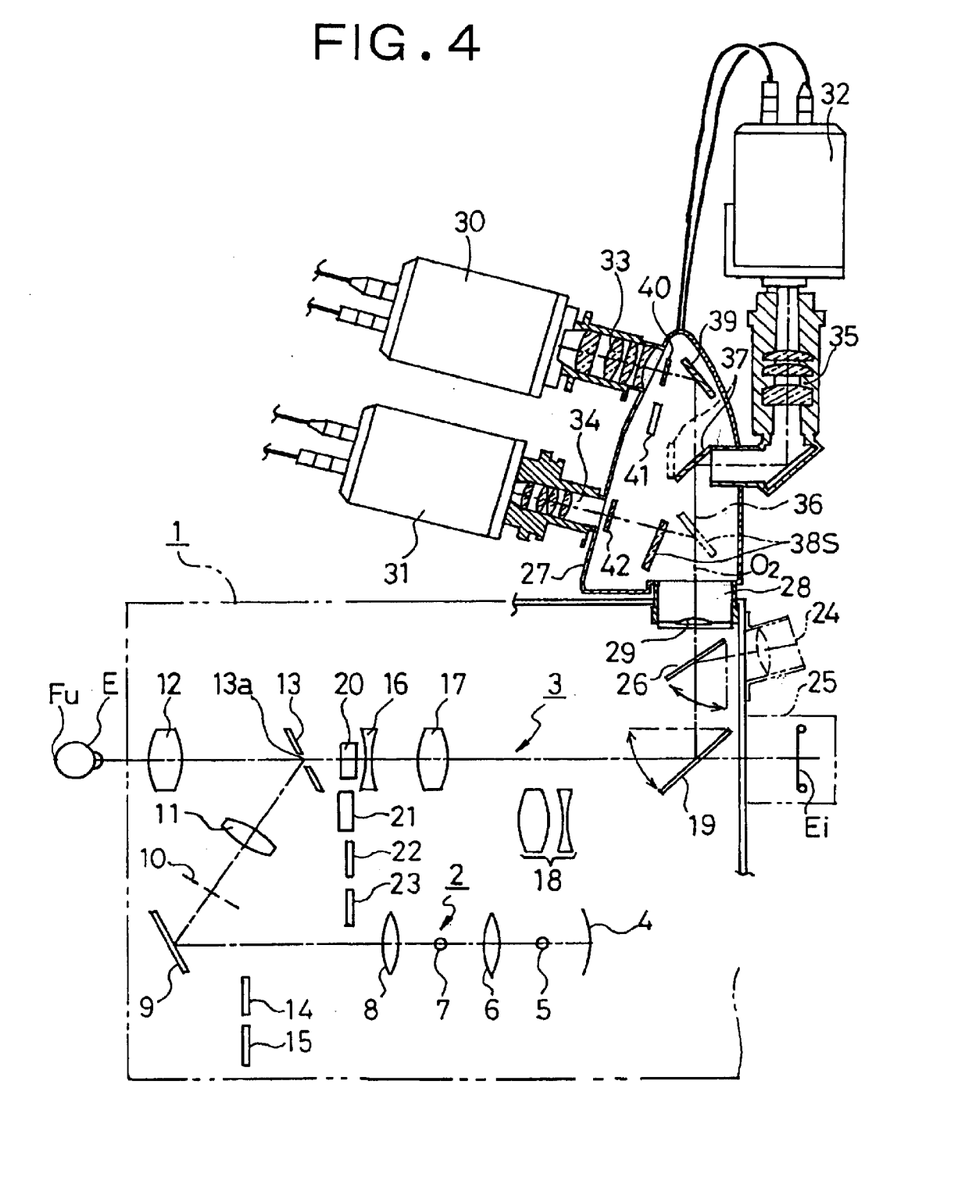
FIG. 4 is a side view with cross-section in part of a Modification No. 4 of fundus camera in accordance with the present invention showing elementary disposition.

In this case within the TV relay lens unit 27, the switching mirrors 38S and 37, and the reflecting mirror 39 are arranged in the optical path O2 in this order from bottom to top as shown in FIG. 4. The color photographing TV camera 31, the observing TV camera 32 and the still image recording TV camera 30 are attached to the body of TV relay lens unit 27 in this order from bottom to top.

In the fundus camera in accordance with this Modification 4 the switching mirror 38S is inserted into the optical path O2 and the fundus image forming luminous flux is directed to the color photographing TV camera 31 when color photographing mode is selected.

When visible-fluorescent photographing mode is selected, the switching mirrors 37 and 38S are retracted from the optical path O2 and then the fundus image forming luminous flux is directed to the still image recording TV camera 30.

When infrared-fluorescent photographing mode is selected and the fundus Fu is observed, the switching mirror 37 is inserted into the optical path O2 and at the same time the switching mirror 38S is retracted from the optical path O2, then the infrared-fluorescent fundus image is directed to the observing TV camera 32. When photographing the fundus Fu under infrared fluorescent photographing mode, the switching mirror 37 as the quick return mirror is instantaneously retracted from the optical path O2 in response to the operation of the shutter releasing button (not shown), and the infrared-fluorescent fundus image is directed to the still image recording TV camera 30.

Modification 5

Another disposition described below can be employed for the fundus camera in accordance with the present invention.

Figure 5:
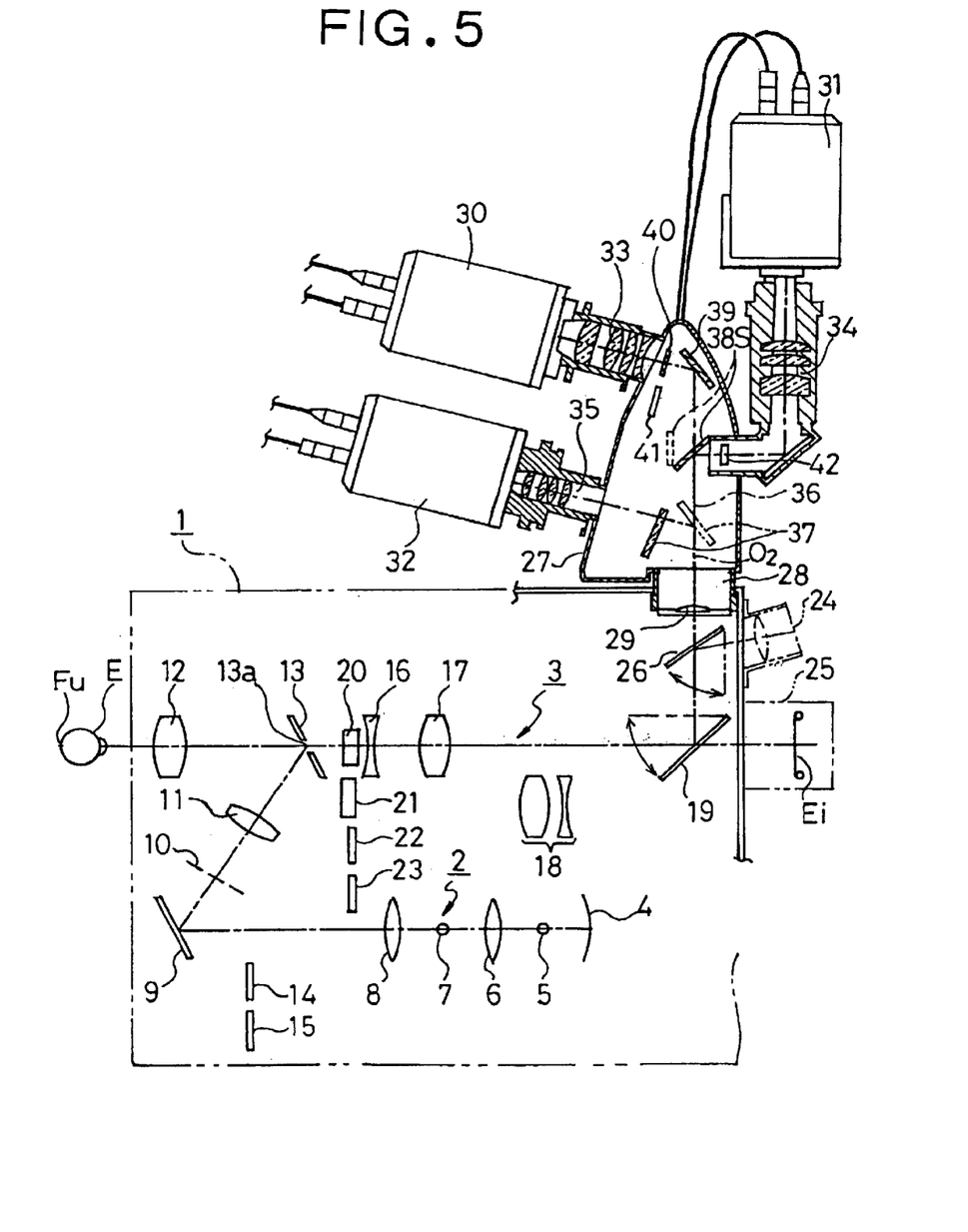
FIG. 5 is a side view with cross-section in part of a Modification No. 5 of fundus camera in accordance with the present invention showing elementary disposition.

In this case within the TV relay lens unit 27, the switching mirror 37, the switching mirror 38S, the reflecting mirror 39 are arranged in this order from bottom to top as shown in FIG. 5. The observing TV camera 32, the color photographing TV camera 31 and the still image recording TV camera 30 are attached to the body of TV relay lens unit 27 in this order from bottom to top. In the fundus camera in accordance with this Modification 5 the switching mirror 37 is retracted from the optical path and the switching mirror 38S is inserted into the optical path O2, then the fundus image forming luminous flux is directed to the color photographing TV camera 31 in color photographing mode.

When visible-fluorescent photographing mode is selected, the switching mirrors 37 and 38S are retracted from the optical path O2 and the fundus image forming luminous flux is directed to the still image recording TV camera 30.

When infrared-fluorescent photographing mode is selected and the fundus Fu is observed, the switching mirrors 37 is inserted into the optical path O2 and the switching mirror 38S is retracted from the optical path O2, then the infrared-fluorescent fundus image is directed to the observing TV camera 32. When photographing the fundus Fu under the infrared fluorescent mode, the switching mirror 37 as the quick return mirror is instantaneously retracted from the optical path O2 in response to the operation of the shutter releasing button (not shown) and the infrared-fluorescent fundus image is directed to the still image recording TV camera 30.

Modification 6

Other disposition described below can be employed further.

Figure 6:
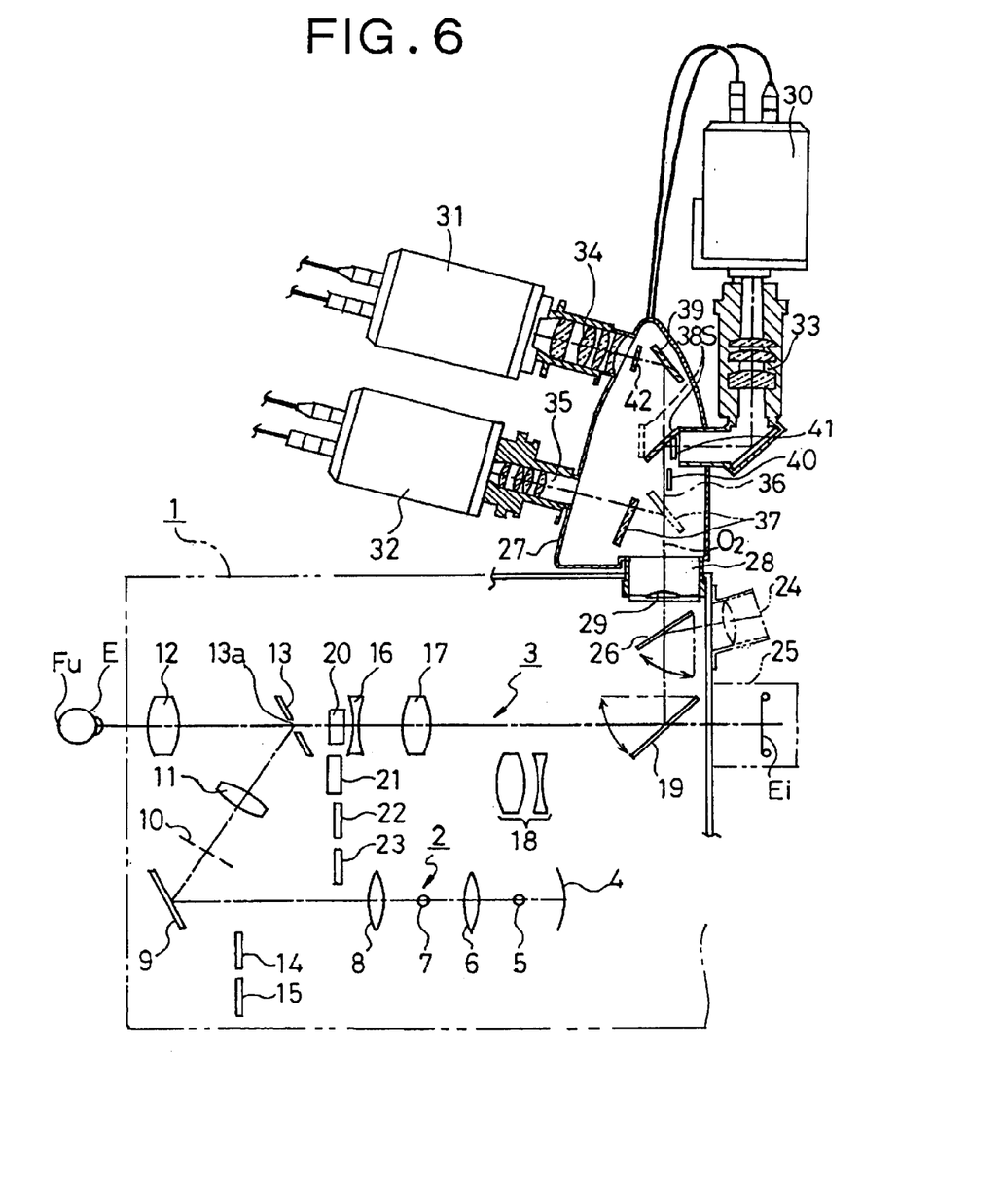
FIG. 6 is a side view with cross-section in part of a Modification No. 6 of fundus camera in accordance with the present invention showing elementary disposition.

In this case within the TV relay lens unit 27, the switching mirrors 37 and 38S, and the reflecting mirror 39 are arranged in this order from bottom to top as shown in FIG. 6. The observing TV camera 32, the still image recording TV camera 30 and the color photographing TV camera 31 are attached to the body of TV relay lens unit 27 in this order from bottom to top.

In the fundus camera in accordance with this Modification 6 the switching mirrors 37 and 38S are retracted from the optical path O2 and the fundus image forming luminous flux is directed to the color photographing TV camera 31 when color photographing mode is selected.

When visible-fluorescent photographing mode is selected, the switching mirror 37 is retracted from the optical path O2 and the switching mirror 38S is inserted into the optical path O2, then the fundus image forming luminous flux is directed to the still image recording TV camera 30.

When infrared-fluorescent photographing mode is selected and the fundus Fu is observed the switching mirrors 37 and 38S are inserted into the optical path O2 and the infrared-fluorescent fundus image is directed to the observing TV camera 32. When photographing the fundus Fu under the infrared fluorescent mode, the switching mirror 37 as the quick return mirror is instantaneously retracted from the optical path O2 in response to the operation of the shutter releasing button (not shown), and the infrared-fluorescent fundus image is directed to the still image recording TV camera 30.

The respective movement of switching mirrors 37 and 38S for above described embodiment and Modifications 1 to 6 is summed up in the following Table 1.

Table 1

In the fundus camera in accordance with the present invention it is not necessary to exchange respective TV cameras according to the photographing mode selected and the operationality has been much improved by means of above described arrangement and disposition.

TABLE 1

Position of Switching Mirror 37 and Optical Element 38 at Optical path O2

| Mode | color 37 | 38 | visible/ fluorescence 37 | 38 | infrared fluorescence (observation) 37 | 38 | infrared fluorescence (photograph) 37 | 38 | FIG. |
|---|---|---|---|---|---|---|---|---|---|
| Embodiment | retracted | | inserted | | retracted | | instantaneously inserted | | 1 |
| Modification 1 | retracted | | inserted | | retracted | | instantaneously inserted | | 1 |
| Modification 1' | retracted | retracted | inserted | any | retracted | inserted | instantaneously inserted | any | 1 |
| Modification 2 | retracted | | inserted | | retracted | | instantaneously inserted | | 2 |
| Modification 3 | any | inserted | inserted | retracted | retracted | retracted | instantaneously inserted | retracted | 3 |
| Modification 4 | any | inserted | retracted | retracted | inserted | retracted | instantaneously retracted | retracted | 4 |
| Modification 5 | retracted | inserted | retracted | retracted | inserted | any | instantaneously retracted | retracted | 5 |
| Modification 6 | retracted | retracted | retracted | inserted | inserted | any | instantaneously retracted | inserted | 6 |

What is claimed is:

1. A fundus camera comprising:

a body unit having photographing optical system to photograph a fundus to be observed; and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected, and a color photographing TV camera having sensitivity for visible light, wherein said TV relay lens unit is equipped with a switching mirror which is retractably and insertably arranged in an optical path of said fundus image forming luminous flux for switching said color photographing TV camera and said visible-fluorescent photographing/infrared-fluorescent photographing TV camera in accordance with the photographing mode;

and a reflecting optical element which is arranged between said switching mirror and said color photographing TV camera to direct said fundus image forming luminous flux to said fundus observing TV camera, and said switching mirror is retracted from the optical path of said fundus image forming luminous flux to direct said flux to said fundus observing TV camera when observing a fundus in said infrared-fluorescent photographing mode, and said switching mirror is instantaneously inserted into said optical path to direct said fundus image forming luminous flux to said visible-fluorescent photographing/infrared-fluorescent photographing TV camera when photographing the fundus in said infrared-fluorescent photographing mode.

2. A fundus camera according to claim 1 characterized in that said reflecting optical element is a dichroic mirror which is selectively passing visible light and reflecting infrared light.

3. A fundus camera according to claim 1 characterized in that said reflecting optical element is a half mirror.

4. A fundus camera according to claim 1 characterized in that said reflecting optical element is a switching mirror which is insertably or retractably arranged in said optical path to direct said fundus image forming luminous flux to said fundus observing TV camera when it is inserted in said optical path.

5. A fundus camera comprising: a body unit having photographing optical system to photograph a fundus to be observed; and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected, and a color photographing TV camera having sensitivity for visible light, and wherein said TV relay lens unit is equipped with first switching mirror which is retracted from the optical path of said fundus image forming luminous flux to direct said fundus image forming luminous flux to said the observing TV camera when infrared-fluorescent photographing mode is selected and the observation thereof is conducted and is instantaneously inserted into the optical path of said fundus image forming luminous flux to direct said fundus image forming luminous flux to said visible-fluorescent photographing/infrared-fluorescent photographing TV camera when infrared-fluorescent photographing mode is selected for photographing the fundus, and second switching mirror which is inserted into the optical path of said fundus image forming luminous flux when color photographing mode is selected, and is retracted from the optical path of said fundus image forming luminous flux when visible-fluorescent photographing mode is selected.

6. A fundus camera comprising:

a body unit having photographing optical system to photograph a fundus to be observed; and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected and a color photographing TV camera having sensitivity for visible light, and wherein said TV relay lens unit is equipped with first switching mirror which is inserted into the optical path of said fundus image forming luminous flux to direct said fundus image forming luminous flux to said the observing TV camera when infrared-fluorescent photographing mode is selected and the observation thereof is conducted, and is instantaneously retracted from the optical path of said fundus image forming luminous flux to direct said fundus image forming luminous flux to said visible-fluorescent photographing/infrared-fluorescent photographing TV camera when infrared-fluorescent photographing mode is selected for photographing the fundus, and second switching mirror which is inserted into the optical path of said fundus image forming luminous flux when color photographing mode is selected and is retracted from the optical path of said fundus image forming luminous flux when visible-fluorescent photographing mode is selected.

7. A fundus camera comprising:

a body unit having photographing optical system to photograph a fundus to be observed; and TV relay lens unit which is detachably mounted on said body unit and having a function to direct a fundus image forming luminous flux from said photographing optical system to plurality of TV cameras, wherein said TV relay lens unit is arranged to be mountable simultaneously a visible-fluorescent photographing/infrared-fluorescent photographing TV camera having sensitivity for both of visible light and infrared light, a fundus observing TV camera having sensitivity for infrared light to observe a fundus when infrared-fluorescent photographing mode is selected and a color photographing TV camera having sensitivity for visible light, and wherein said TV relay lens unit is equipped with first switching mirror which is inserted into the optical path of said fundus image forming luminous flux to direct said fundus image forming luminous flux to said the observing TV camera when infrared-fluorescent photographing mode is selected and observation thereof is conducted, and is instantaneously retracted from the optical path of said fundus image forming luminous flux to direct said fundus image forming luminous flux to said visible-fluorescent photographing/infrared-fluorescent photographing TV camera when infrared-fluorescent photographing mode is selected for when photographing the fundus, and second switching mirror which is retracted from the optical path of said fundus image forming luminous flux when color photographing mode is selected and is inserted into the optical path of said fundus image forming luminous flux when visible-fluorescent photographing mode is selected.

* * * * *